United States Patent [19]

Hieftje et al.

[11] Patent Number: 5,335,860
[45] Date of Patent: Aug. 9, 1994

[54] ROTARY SPRAY CHAMBER DEVICE FOR CONDITIONING AEROSOLS

[75] Inventors: Gary M. Hieftje; Min Wu, both of Bloomington, Ind.

[73] Assignee: Indiana University Foundation, Bloomington, Ind.

[21] Appl. No.: 1,815

[22] Filed: Jan. 8, 1993

[51] Int. Cl.$^5$ ............................................. B05B 1/34
[52] U.S. Cl. ................................... 239/469; 239/468; 239/499; 239/548; 210/512.1; 210/788; 73/863.21
[58] Field of Search ............... 239/124, 461, 463, 468, 239/469, 499, 548; 250/288; 210/788, 512.1; 73/863.21

[56] References Cited

U.S. PATENT DOCUMENTS

| | | | |
|---|---|---|---|
| 1,639,685 | 8/1927 | Coffey et al. | 239/468 X |
| 1,938,000 | 12/1933 | Wahlin | 239/468 |
| 4,570,494 | 2/1986 | Dunn et al. | 73/863.21 X |
| 4,673,656 | 6/1987 | Pink . | |
| 4,743,407 | 5/1988 | Apel et al. . | |
| 4,793,556 | 12/1988 | Sharp . | |
| 4,941,618 | 7/1990 | Hildebrand et al. . | |
| 5,112,498 | 5/1992 | Davies | 210/788 X |
| 5,162,650 | 11/1992 | Bier | 250/288 |
| 5,163,617 | 11/1992 | Clifford et al. . | |
| 5,202,562 | 4/1993 | Koga et al. | 250/288 X |

OTHER PUBLICATIONS

R. F. Browner, pp. 244–288, "Inductively coupled plasma emission spectroscopy, Part II: Applications and Fundamentals", Edited by P. W. J. M. Boumans, John Wiley & Sons, 1987.
B. L. Sharp, J. Anal. At. Spectrom, vol. 3, pp. 939–963 (Oct. 1988).
G. Vujicic and I. Steffan, Spectrochim. Acta, vol. 43B, pp. 293–294 (1988).
K. A. Vermeiren et al. J. Anal. At. Spectrom., vol. 3, pp. 571–577 (Jun. 1988).
C. A. Monnig et al., Spectrochim. Acta, vol. 43B, pp. 261–270 (1990).
L. Ebdon et al. J. Anal. At. Spectrom. vol. 4, pp. 505–508 (Aug. 1989).
H. Isoyama et al., J. Anal. At. Spectrom. vol. 4, pp. 351–355 (Jun. 1989).
A. J. Ambrose et al., J. Anal At. Spectrom., vol. 4, pp. 219–222 (Mar. 1989).

Primary Examiner—Andres Kashnikow
Assistant Examiner—William Grant
Attorney, Agent, or Firm—Woodard, Emhardt, Naughton, Moriarty & McNett

[57] ABSTRACT

Described is a preferred rotary spray chamber device for conditioning an aerosol. The device has chamber walls defining an internal chamber and an inlet opening into the internal chamber. The inlet opening is located such that an aerosol directed into the chamber through the inlet opening tangentially contacts chamber wall areas adapted to impart a rotary motion to the aerosol within the chamber. An impact member extends inwardly into the chamber from a chamber wall location such that the member is impacted by the aerosol in its rotary motion so as to remove large droplets and thus form a conditioned aerosol. An exit opening is defined by the chamber walls through which the conditioned aerosol can exit the chamber, and a drain opening is also defined by the chamber walls through which liquid removed from the aerosol and collected in the chamber can exit the chamber.

22 Claims, 9 Drawing Sheets

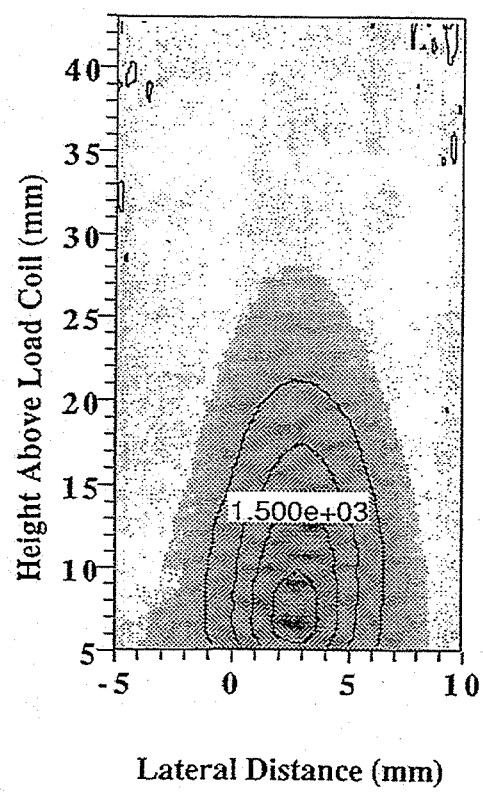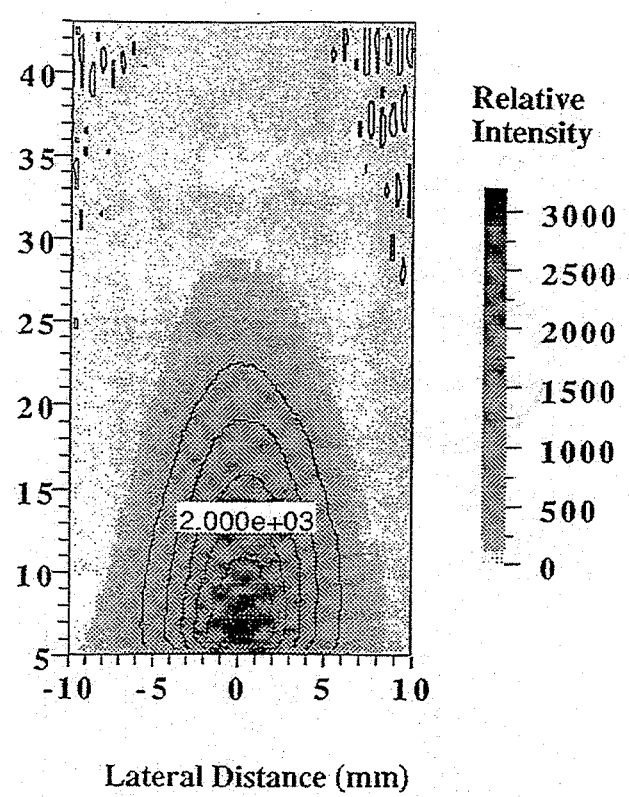
Fig. 7A
Fig. 7B

ROTARY SPRAY CHAMBER DEVICE FOR CONDITIONING AEROSOLS

BACKGROUND

The present invention relates generally to a device for conditioning an aerosol such as that resulting from the nebulization of a liquid sample, and more particularly to a device for removing large droplets from an aerosol stream so as to enable improved stability of analytical signals derived from the aerosol.

Since the early days of flame emission spectrometry, it has been realized that a spray chamber placed between the nebulizer and burner could function as a droplet separator and a flow buffer to remove large droplets from the sample aerosol and thereby improve the stability of analytical signals derived from the aerosol. Usually such spray chambers were made from available laboratory glassware. Yet, even these relative crude early designs were so effective that similar spray chamber units are still commonly employed today in atomic absorption and flame emission instrumentation. These spray chambers were later scaled down, somewhat modified and adapted to use in inductively coupled plasma spectrometry.

In all of these spray chambers, the removal of large droplets is inevitably accompanied by a reduction in the transport efficiency of aerosol and analyte to the subsequent atomization/excitation source. For example, measurements carried out on a typical inductively coupled plasma (ICP) nebulizer/spray chamber system reveal that more than 98% of the aerosol is lost to waste. As a result, the transport efficiency of a typical ICP system is only in the range of about 0.5%–2%. Also, fine droplets are suspended and circulate inside the spray chamber, resulting in relatively long wash-out times. For a typical system, it usually takes several minutes to change a sample. Such recognized low transport efficiencies and large memory effects have existed in atomic spectrometry for nearly a half century and they remain among the weak links in the field.

Continuing efforts have been made to improve nebulizer/spray chamber systems. Single- and double-barrel Scott-type spray chambers, cyclone configurations, baffles, and gravitational sedimentation chambers have been used in inductively coupled plasma emission spectrometry (ICP-AES). Other techniques have also been explored to circumvent conventional nebulizer-spray chamber systems. For example, jet-impact and direct-injection nebulization have been used with inductively coupled plasma emission and mass spectrometry. Fundamental investigations into aerosol characterization have offered some insight into the performance of aerosol chambers and its dependence on centrifugal force, evaporation, gravitation, impaction, and turbulence. Nevertheless, there still exists a need for improved spray chambers providing increased throughput and stability to analytical signals derived from sample aerosols. The present invention addresses this need.

SUMMARY OF THE INVENTION

The present invention relates to a novel spray chamber device incorporating gravitational, centrifugal, turbulent and impact aerosol-sizing mechanisms in a single apparatus. One preferred embodiment of the invention thus provides a rotary spray chamber device for conditioning an aerosol. The rotary spray chamber device comprises chamber walls defining an internal chamber, an inlet opening through which aerosol can be directed into the internal chamber, an exit opening through which aerosol can exit the chamber, and a drain opening through which liquid removed from the aerosol and collected in the chamber can exit therefrom. The inlet opening is located so that an aerosol directed into the chamber through the inlet opening tangentially contacts chamber wall areas adapted to impart a rotary motion to the aerosol within the chamber. A impact member extends inwardly into the chamber from a chamber wall location such that the impact member is impacted by the aerosol in its rotary motion so as to remove large droplets from the aerosol and thus form a conditioned aerosol.

In a more preferred embodiment, the device includes a hollow generally flattened spheroid member having opposed side walls and which which defines the internal chamber. An inlet opening is defined in the flattened spheroid member and positioned so that an aerosol directed into the inlet opening tangentially contacts interior walls of the flattened spheroid member which impart a rotary motion to the aerosol within the chamber. A dimple in one of the side walls provides an impact member adapted to condition the rotating aerosol by removing large droplets therefrom. An exit opening is defined in the other of the side walls of the flattened spheroid member through which the conditioned aerosol can exit the chamber. Further, a drain opening is defined in the flattened spheroid member through which liquid removed from the aerosol and collected in the chamber can be drained from the chamber.

Another preferred embodiment of the present invention provides an apparatus for producing a conditioned aerosol from a liquid. An apparatus for conditioning a liquid sample for analysis, comprising a nebulizer adapted to form a nebulized stream from the liquid sample. A rotary spray chamber for conditioning the nebulized stream, the rotary spray chamber including chamber walls defining an internal chamber and an inlet opening into the internal chamber, inlet opening being so located that a nebulized stream of liquid passed into the chamber through the inlet opening tangentially contacts chamber wall areas so as to impart a rotary motion to the nebulized stream within the chamber. A dimple member extending inwardly into the chamber from a chamber wall location such that the dimple is contacted by the nebulized stream in its rotary motion so as to remove large droplets from the nebulized stream and thus form a conditioned nebulized stream. An exit opening defined by the chamber walls through which the conditioned nebulized stream can exit the chamber, and a drain opening defined by the chamber walls through which liquid removed from the nebulized stream and collected in the chamber can exit the chamber, and means for directing the nebulized stream from the nebulizer into the inlet opening of the rotary spray chamber.

Additional preferred embodiments relate to methods for conditioning aerosol sprays as embodied in the discussion below.

As demonstrated herein, the rotary spray chamber of the present invention provides superior aerosol conditioning characteristics, including for instance a combination of low memory effects, high transport efficiency, minimal backing pressure fluctuation, and excellent figures of merit. Furthermore, the device is compact, inexpensive and easily manufactured.

Additional objects, features and advantages of the present invention will be apparent from the description herein.

BRIEF DESCRIPTION OF THE DRAWINGS

FIG. 7 shows maps of blank-subtracted MgII 280.27 nm emission intensities from an optimized 23-nm plasma for the Scott-type 7A (left) and inventive-rotary 7B (right) spray chambers.

DESCRIPTION OF THE PREFERRED EMBODIMENT

Figure 1:
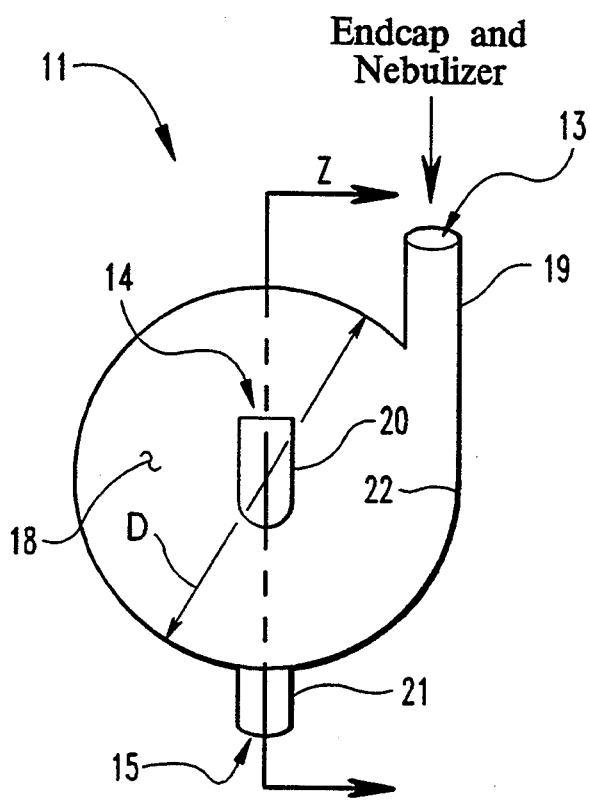
FIG. 1 is a front view of a rotary spray chamber device of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention pertains.

Figure 2:
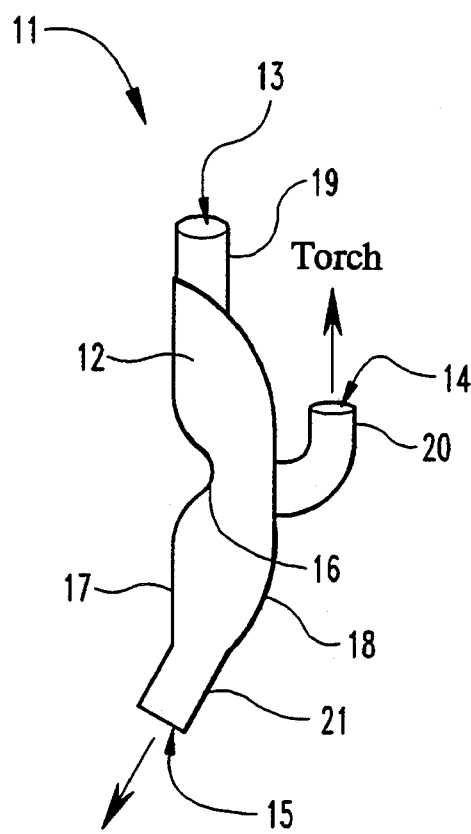
FIG. 2 is cross-sectional view of the the rotary spray chamber device of FIG. 1, taken along line Z—Z and viewed in the direction of the arrows.

A preferred rotary spray chamber device of the present invention is illustrated in FIGS. 1 and 2. Briefly describing the preferred device, the spray chamber is advantageously constructed from Pyrex borosilicate glass and has the general shape of an elipsoid such as a flattened spheroid with a generally symmetrical axis horizontal when the major axis of the flattened spheroid is positioned vertically (as illustrated in FIGS. 1 and 2). Sample solution is introduced through a nebulizer device, for example a concentric pneumatic nebulizer aimed downward and intersecting the chamber tangentially, to generate a rotary or centrifugal action of the aerosol. This swirling action serves to remove large droplets from the aerosol. The drainage outlet is generally located at the bottom of the chamber when in use to promote rapid escape of collected liquids to the waste bottle. The drainage outlet is preferably relatively small in size so as to prevent air from leaking into the chamber.

In the preferred device illustrated, a dimple is located in the side of the generally cylindrical chamber of the flattened spheroid, to further aid in the removal of large droplets from the aerosol. The utility of the dimple was determined by sending into the chamber an expanded sheet of light from a He-Ne laser. The thin plane of light, viewed from the side, permitted the swirling pattern of droplets inside the chamber to be viewed directly. In the absence of the dimple, scattered light from large droplets was clearly apparent, whereas large droplets could not be seen in the dimpled chamber. This evidences the achievement of an advantageous reduction in the cut-off diameter of droplets in the conditioned aerosol eventually leaving the spray chamber.

Referring now to FIGS. 1-3, the preferred rotary spray chamber device 11 and its use will be more particularly described. FIG. 1 provides a front view of a rotary spray chamber device 11 according to the invention. FIG. 2 provides a side view of the rotary spray chamber device 11 of FIG. 1. FIG. 3 provides an illustration of a drainage tube device 23 which can be connected to the drain of the rotary spray chamber device 11.

Referring first specifically to FIGS. 1 and 2, the preferred rotary spray chamber device 11 has walls defining a generally cylindrical internal chamber 12. The rotary spray chamber device 11 also has an inlet opening 13, an outlet opening 14, and a drainage opening 15. Openings 13, 14 and 15 are in spaced apart relationship to each other, and open into the internal chamber 12. The rotary spray chamber device 11 has an impact member 16, preferably generally conical or spheroid or partial spheroid in shape (e.g. hemi-spheroid), extending inwardly into the chamber 12. The impact member 16 can be, for example, provided by a dimple formed in wall portions defining the chamber 12.

The preferred device 11 has a generally elipsoid shape, more preferably a flattened spheroid as illustrated with side walls 17 and 18. The preferred rotary spray chamber device 11 also has an inlet tube member 19, an outlet tube member 20, and a tubular drain member 21, each preferably cylindrical in shape and each providing fluid connection between the internal chamber 12 and locations exterior thereof.

As can be seen from FIGS. 1 and 2, inlet opening 13 is positioned such that an aerosol directed through the inlet opening 13 tangentially contacts walls of the chamber 12, such as at position 22 (FIG. 1), so as to impart a rotary or cyclonic motion to the aerosol within the chamber 12, preferably rotating substantially in a plane parallel to the major axis of the spray chamber 12 (i.e. rotating generally in a vertical plane when the device 11 is oriented as in the Figures). The drain opening 15 is desirably located at or near one of the ends of the device 11 along its major axis. In this manner, the device 11 can be utilized with its major axis in a vertical position (as illustrated) as is preferred, while conveniently draining collected liquid from the bottom of the device 11.

The impact member 16 is located and adapted so as to be impacted by the aerosol in its rotary motion and remove larger droplets from the aerosol. In this regard, the impact member 16 preferably extends into the chamber in a direction perpendicular to the rotation of the aerosol. Further, the impact member 16 is preferably centrally located on the sidewall of the flattened spheroid, so that the rotary motion of the aerosol is generally about the impact member 16.

As can also be seen from the Figures, the exit opening 14 from the chamber 12 is preferably located in the opposite side wall from the impact member 16 (side wall 18), substantially opposite the location of the impact member 16. A preferred device has a diameter "D" (FIG. 1) of approximately 10 cm or less, more preferably about 6 cm or less, and can in further preferred embodiments even smaller, e.g. about 4 cm or less. The volume of the chamber 12 of the device is preferably about 50 ml or less, more preferably about 25 ml or less, and can in further preferred embodiments be about 15 ml or less. Such small volumes facilitate advantageously quick wash-out times.

Figure 1A:
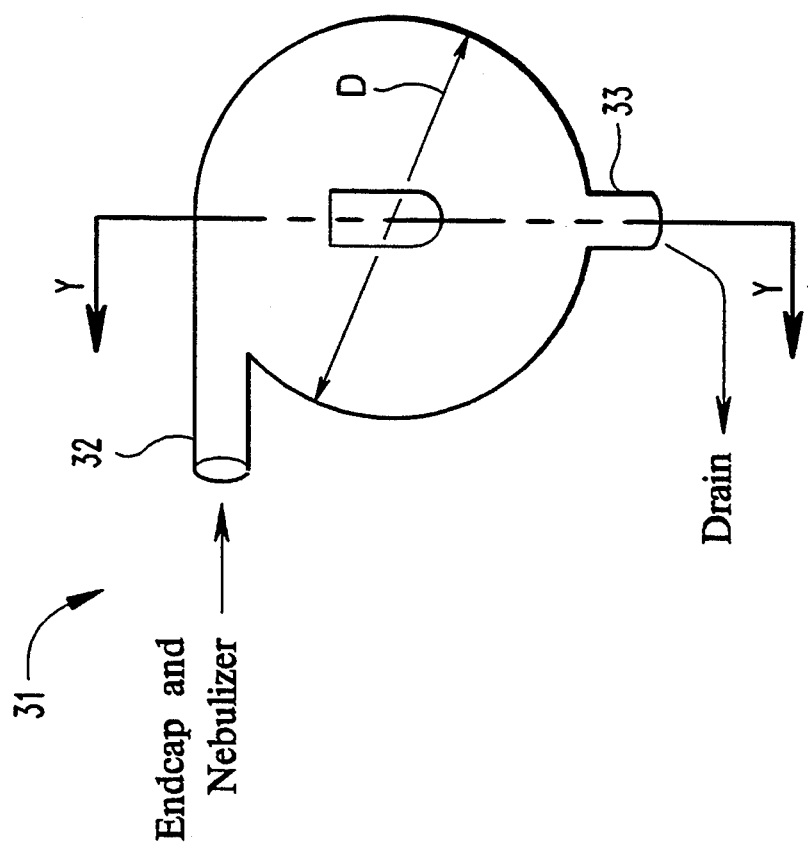
FIG. 1A is a front view of an alternative configuration for a rotary spray chamber device of the present invention.

Referring now to FIGS. 1A and 1B, shown is an alternative rotary spray chamber device 31 in accordance with the invention. The device is similar to spray chamber 11 of FIGS. 1 and 2, but having differing orientations of the inlet and drainage openings. As can be seen, the axis of the inlet opening and its tube 32 is perpendicular to the axis of the drainage outlet and its tube 33. Thus, when the device is positioned having the axis of drainage tube 33 vertically oriented, the axis of the inlet tube 32 is horizontally disposed, thus allowing for horizontal input of aerosol into the chamber.

Figure 3:
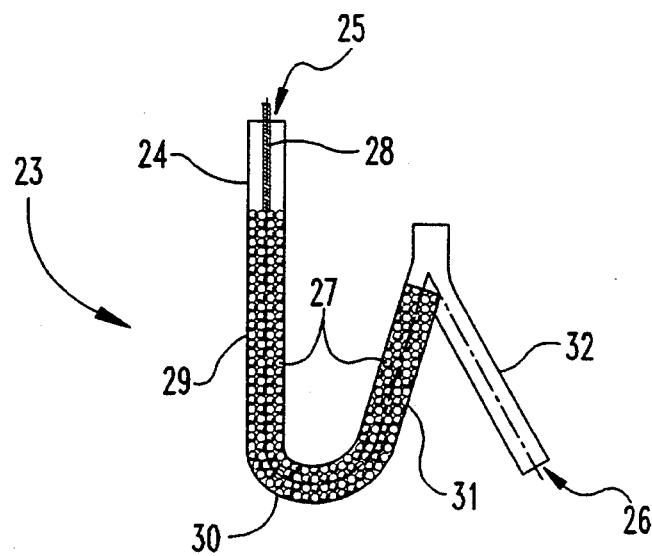
FIG. 3 illustrates a drainage tube device that can be used in conjunction rotary spray chamber devices of the present invention.
Figure 2A:
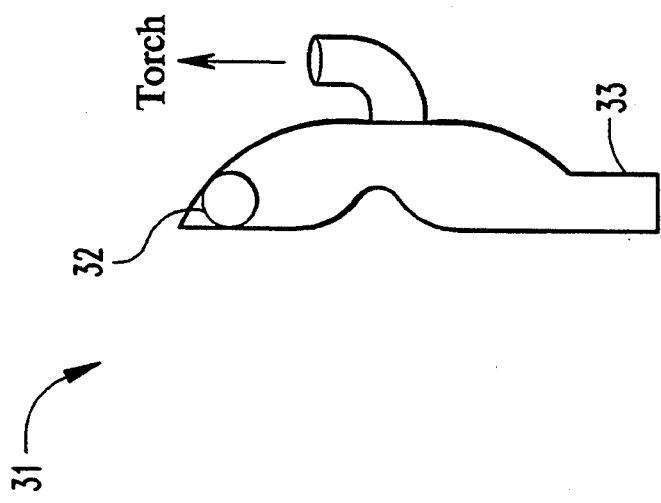
FIG. 2A is cross-sectional view of the the rotary spray chamber device of FIG. 1A, taken along line Y—Y and viewed in the direction of the arrows.

Referring now to FIG. 3, shown is a drainage tube device 23 which can be connected to the drainage opening 15 of the rotary spray chamber device 11 (FIG. 2). The drainage tube device 23 is made from generally tubular member 24, advantageously formed of Pyrex glass. The device 23 has an inlet opening 25 and an outlet opening 26. Further, contained within the tubular member 24 are spherical beads 27, for example made of glass, and a wick 28 formed from a suitable wicking material such as cotten or another cloth. The wick 28 extends above the level of the beads 27 within the tubular material 24, so that when the drainage tube device 23 is coupled to the drain opening of the rotary spray chamber device 11, the wick lies within or nearly within the drainage opening 15 of the device 11 (FIG. 2). In this manner, the wick 28 helps induction of the collected liquid out of the chamber 12 to prevent substantial liquid accumulation therein.

Generally as to its shape, the drainage tube device 23 has a substantially straight portion 29 terminating in a "U" shaped curved portion 30 and extending into another generally straight portion 31. In turn, portion 31 extends to a generally downwardly extending portion 32, such that portions 31 and 32 in combination resemble an inverted "V". The drainage tube device 23 helps to overcome pressure pulsations.

In use, the drainage tube device 23 is fluidly connected to the rotary spray chamber 11 at its drainage tube member 21 so as to leave the wick 28 near or in drainage tube 21. The exit opening via its exit tube member 20 is fluidly connected to the torch or other sample treatment means of the analysis device involved. The inlet tube member 19 of the inlet opening is fluidly connected to a nebulizer device.

Figure 10:
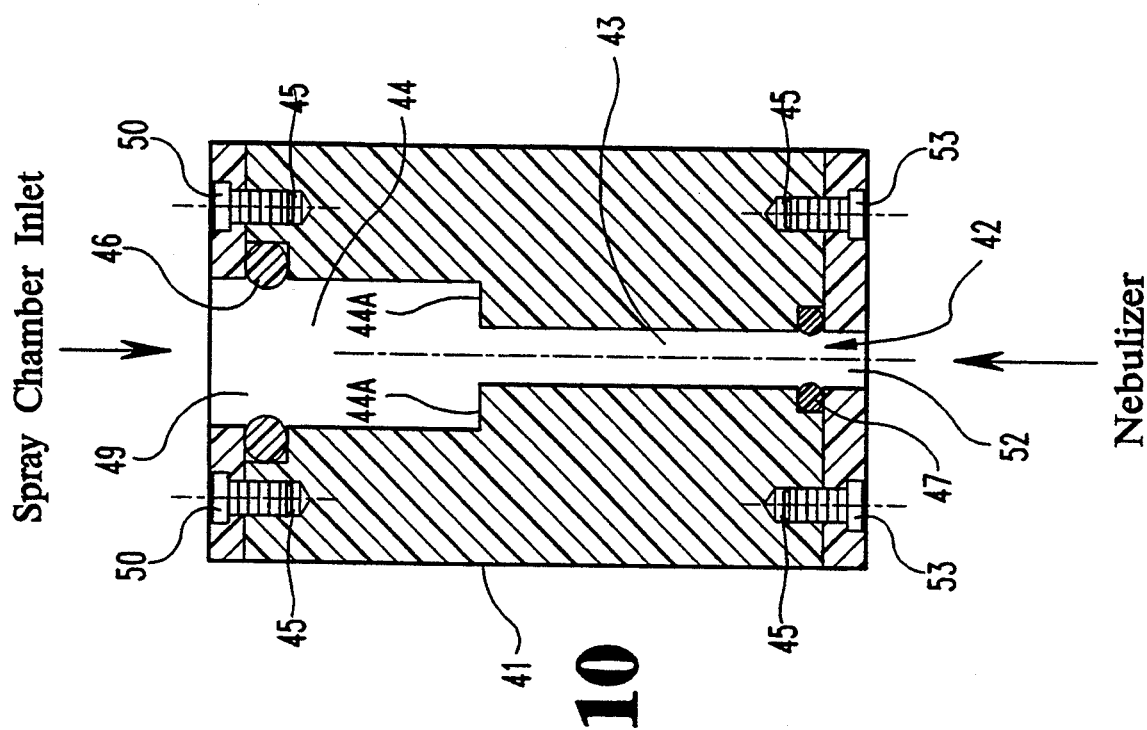
FIG. 10 is a cross-sectional view of the encap of FIG. 9 taken along line X—X and viewed in the direction of the arrows.
Figure 9:
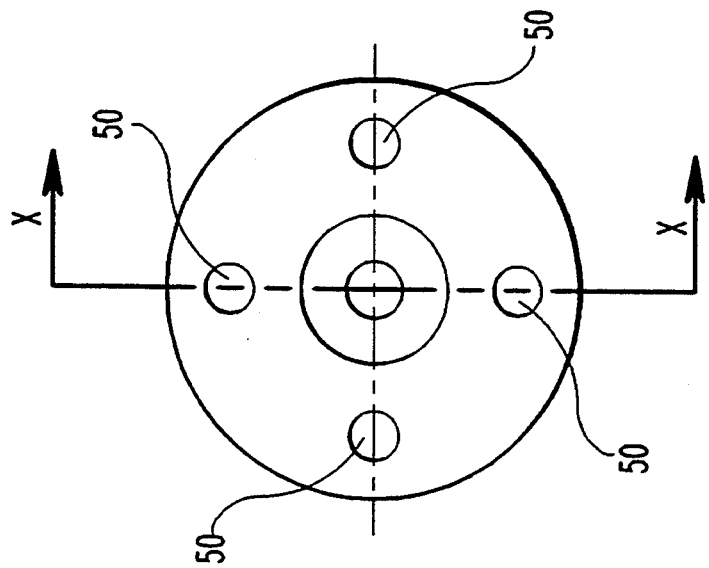
FIG. 9 provides a top view of an endcap for fluidly connecting rotary spray chambers of the invention to nebulizers.

In this regard, reference is made to FIGS. 9 and 10, which illustrate an endcap device which is preferably used to connect inlet tube member 19 to the nebulizer device. The endcap device includes a connector body 41 made of Teflon or another suitable material. The body 41 is generally cylindrical in shape and has a centrally located bore 42, which bore 42 has a smaller diameter portion 43 residing closer to the nebulizer and a larger diameter portion 44 residing closer to the spray chamber 11 and providing internal walls 44A. The connector body 41 also has screw holes 45 located about its periphery. The connector body 41 is used in conjunction with "O"-rings 46 and 47 or similar sealing devices, and with spray chamber inlet ring 48 and nebulizer outlet ring 51, each made of Teflon or another suitable material. The spray chamber inlet ring 48 has a central bore 49 sized to fit over the inlet tube 19 of the spray chamber 11 and screw holes aligned with corresponding screw holes 45 of connector body 41. Similarly, nebulizer outlet ring 51 has a central bore 52 sized to fit over the outlet of the nebulizer and screw holes aligned with corresponding screw holes of connector body 41.

In use, the endcap device is assembled as illustrated, except screws 50 are in a loosened state to eliminate compression of the O-rings 46 and 47. This allows the inlet tube 19 to be placed within the larger bore portion 44 until it abuts internal walls 44A. The screws 50 are then tightened to compress the O-ring 46 in such a manner that it seals against and secures the tube 19. In corresponding fashion, the tube of the nebulizer outlet is placed through bore 52 and bore 42 of the connector body 41, and positioned within the spray chamber 11 as desired. The screws 53 are then tightened to compress O-ring 47 which seals against and secures the nebulizer outlet tube within the spray chamber.

The liquid sample is then passed through the nebulizer so as to form an aerosol which is directed into the device 11 via its inlet opening 13. The aerosol contacts walls of the device 11, for example at location 22, and is caused to have a rotary or cyclone motion generally about the contact member 16. Larger droplets within the aerosol are removed with the aid of the impact member 16 and the centrifugal force caused by the rotary motion. Collected liquid removed from the aerosol is then drained via drainage opening 15 and proceeds through drainage tube device 23 to a waste or other collection unit. The conditioned aerosol then passes out the exit opening 14 via the exit tube 20 and proceeds to tile analytical device involved which can be, for example, an inductively coupled plasma system, or an atomic emission spectrometry system employing a microwave plasma as the atomic emission source. The rotary spray chamber device of the invention can be applied to continuous solution flow analysis in emmission and mass spectrometry (to improve throughput, stability and sensitivity), to flow injection analysis in atomic emission and mass spectrometry (to improve throughput and sensitivity), and as an HPLC or ion chromatographic interface to introduce solution sample into plasma detectors.

To promote a further understanding of the present invention and to demonstrate its advantages, the following experimental examples are provided. It will be understood that these examples are illustrative and not limiting of the invention.

A double-pass Scott-type spray chamber (Model 50 Plasma-Therm, Inc. Kresson, N.J.) with a volume of 200 ml was used for comparison to a rotary spray chamber device of the present invention (dimensions: diameter of device "D"=6 cm; width of chamber=2 cm; dimple diameter=1.5 cm; inlet opening inner diameter=0.8 cm; drainage opening inner diameter=0.5 cm;

exit opening inner diameter=0.5 cm). The outputs of both spray chambers were connected directly to the central tube of an ICP torch as described further below. A drainage device such as that illustrated in FIG. 3 was connected to the drain port of both spray chambers, to overcome pressure pulsations (dimensions: tube inner diameter=0.5 cm; height of device=50 cm; glass bead outer diameter 3 mm; cotton string (wick) outer diameter 0.2 cm.).

Inductively Coupled Plasma System

Two different RF plasma generators were employed in the course of this study, to ensure that observed performance levels were a function of spray-chamber design and not a result of the other instrumental factors. A 27.17 MHz Plasma-Therm RF Generator Model HFP 5000D coupled with an AMNPS-1 impedance marcher was used for the measurement of memory effects, figures of merit and interference effects. Conditions for its operation are compiled in Table 1. A 40- MHz Leco solid-state RF generator was used during the optimization of analyte emission signals; its optimized conditions are also set forth in Table 1.

Reagents

Sample solutions were obtained by diluting 1000 μg/ml stock solutions with distilled, deionized water. The stock solutions were prepared from analytical reagent-grade metals or chloride salts.

Data Acquisition

For analytical measurements, a 150-mm focal-length lens was used to project the plasma image onto the entrance slit of a Heath monochromator (model EU-700). A Keithley (model 414S) picoammeter was used as a current-to-voltage converted and was coupled to a National Instruments NB-MIO-16XL-18 interface board in a Macintosh IIfx computer. A software-configured low-pass filter provided an integration time of 10 seconds. Background and signals were recorded only after their intensity levels were unchanged for at least two minutes.

Transport Efficiency

Silica-gel collection was employed to determine the aerosol-transport efficiency as previously described (see, R. F. Browner, p 244–288, "Inductively coupled plasma emission spectroscopy, Part II: Applications and Fundamentals" Edited by P. W. J. M. Boumans, John Wiley & Sons, 1987). Thus, aerosol and solvent vapor issuing from the spray chamber were passed directly into a U-tube packed with dry silica gel. The weight difference of the U-tube before and after the collection gave the solvent mass flow rate out of the spray chamber. Transport efficiency was calculated as the ratio of the mass of solvent collected by the silca gel and the amount of liquid aspirated into the nebulizer.

Measurements of transport efficiency yield 1.9% for a 16-cm-long double-pass Scott-type spray chamber and 2.8% for the 6-cm diameter vertical rotary spray chamber, both at 0.7 L/min aerosol-gas flow rate and 1.5 mL/min sample uptake rate. The rotary spray chamber demonstrated nearly 50% higher throughput than the Scott-type chamber. Further, the transport efficiency was found to increase slightly with carrier-gas flow rate for both spray chambers.

Memory Effects

Figure 4A:
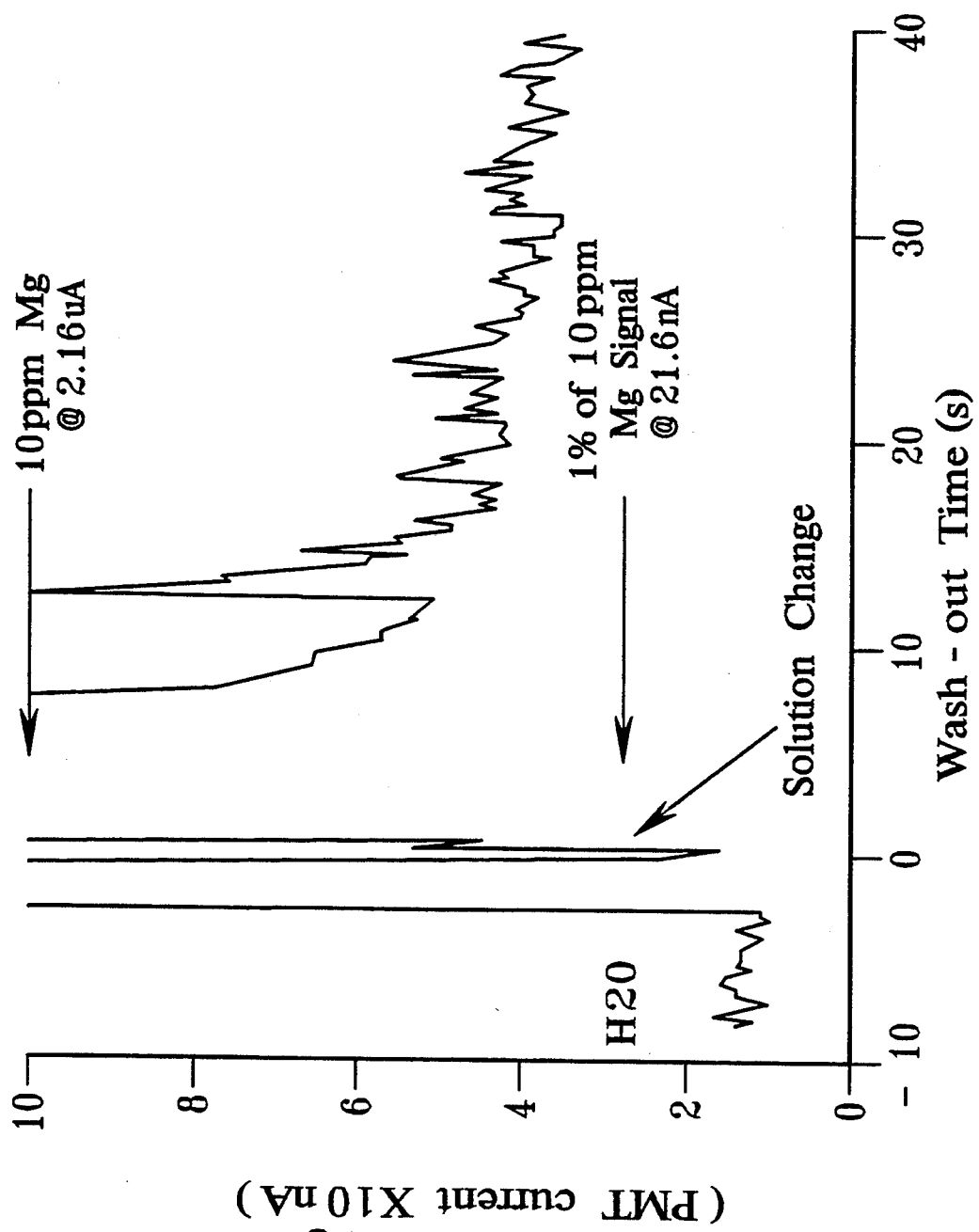
FIG. 4 provides a comparison of wash-out times for (a) a commercially available Scott spray chamber and (b) a rotary spray chamber of the present invention.
Figure 4B:
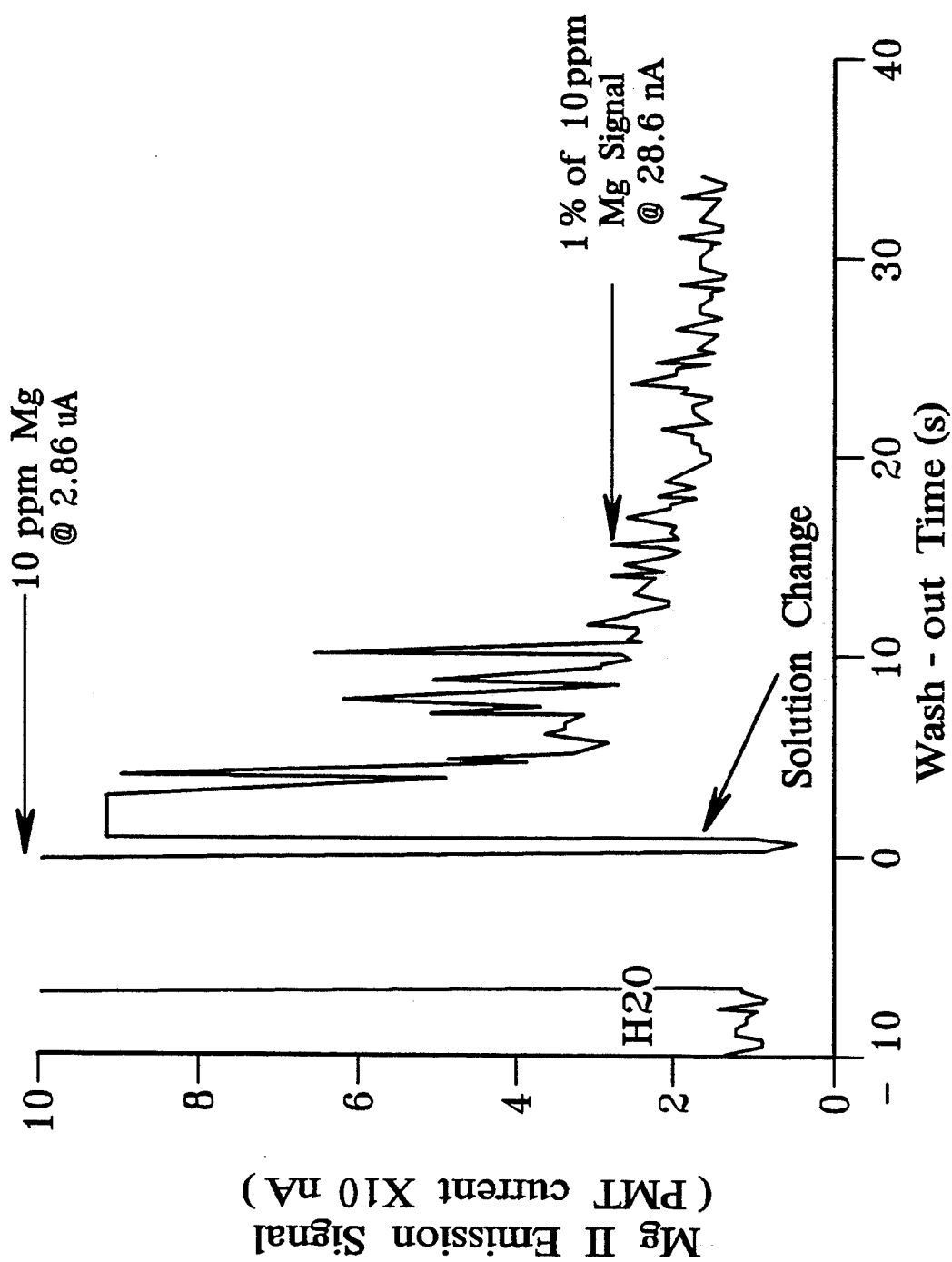

Memory effect can be expressed in terms of the wash-out time of a spray chamber, defined here as the time required for a signal to fall to 1% of its initial value (see, B. L. Sharp, J. Anal. At. Spectrom, Vol. 3, pp. 939 (1988)). A 10 μg/mL solution of Mg was used and produced signal-decay curves of Mg II 280.27 nm emission as illustrated in FIG. 4. The emission from MgII at 280.27 nm was recorded in the range of 2–3 μA and the background emission signal of the blank was in the range of 0.02–0.03 μA (see horizontal arrow). The resulting wash-out time for the Scott chamber is roughly 42 seconds (4(a)) whereas that for the new spray chamber is about 14 seconds (4(b)). The operating conditions of the 27 MHz ICP-AES instrument are listed in Table 1. The mean wash-out times were obtained by averaging three different decay curves and are compiled in Table 2 along with other figures of merit.

A theoretical decay (wash-out) time can be estimated from the residence time of a particle in the spray chamber and from the volume of the chamber. Previous researchers have calculated residence times from the mean bulk gas flow and then have made arbitrary allowances for the velocity lag of particles. If the chamber functions as an ideal mixing volume, its decay time is approximately three times the ratio of the volume of the chamber to the flow rate (see, B. L. Sharp, J. Anal. At. Spectrom, Vol. 3, pp. 939 (1988); and N. Z. Christchurch, Can. J. Chem. Eng., Vol. 55, pp. 466 (1985)). For a Scott-type spray chamber with a volume of 200 mL and a vertical rotary chamber with a volume of 40 mL, both operated with a carrier-gas flow rate of 1 L/min, theoretical decay times are 35 s and 7.2 s, respectively, in fair agreement with the experimental results. Remaining discrepancies can be accounted for by small suspended particles possibly trapped in the recirculating flow and by the convoluted path that aerosol droplets must follow in the Scott chamber.

The inventive rotary spray chamber can be operated in positions varying from horizontal to vertical. However, vertical or substantially vertical orientations are preferred (as were used in the present examples), as they provide shorter wash-out times.

Figures of Merit

Figures of merit were collected on a Macintosh IIfx computer by means of a Lab VIEW 2 program configured to use a National Instruments NB-MIO-16XL-18 interface board. Figures of merit compiled in Table 2 are the averages of three different measurements.

In rough agreement with the transport-efficiency results reported above and with the signal levels in FIG. 4, the Mg II signal recorded in Table 2 is greater by about 35% with the vertical rotary spray chamber than with the Scott chamber. At the same time, the background is reduced slightly. Detection limits can be computed from the ratio of signal to background noise ($S/N_B$) and from the concentration used to produce the measured signal level (10 μg/mL). In particular, $S/N_B$=3270 with the Scott chamber, so $S/N_B$=3 at 9 ppb; $S/N_B$=9150 with the new vertical rotary spray chamber, so $S/N_B$=3 at 3 ppb, a factor of three improvement in detection limit for the inventive rotary spray chamber. Values for RSDS and RSDB obtained in the present study are comparable with those reported earlier (see, P. A. Vieira et al., Appl. Spectrosc., Vol. 40, pp 141 (1986)) and do not differ appreciably between the two spray-chamber designs. Further improvements in precision may be achievable through stabilization of the RF generator and by thermostatic control of the nebulizer-spray chamber system (see, G. Vujicic and I. Steffan, Spectrochim. Acta, Vol. 43B, pp. 293 (1988); K. A. Vermeiren et al., Anal. At. Spectrom., Vol. 3, pp. 571 (1988); and P. Schramel et al., Anal. Chem., Vol. 320, pp. 233 (1988)).

Interference Effects

Figure 5:
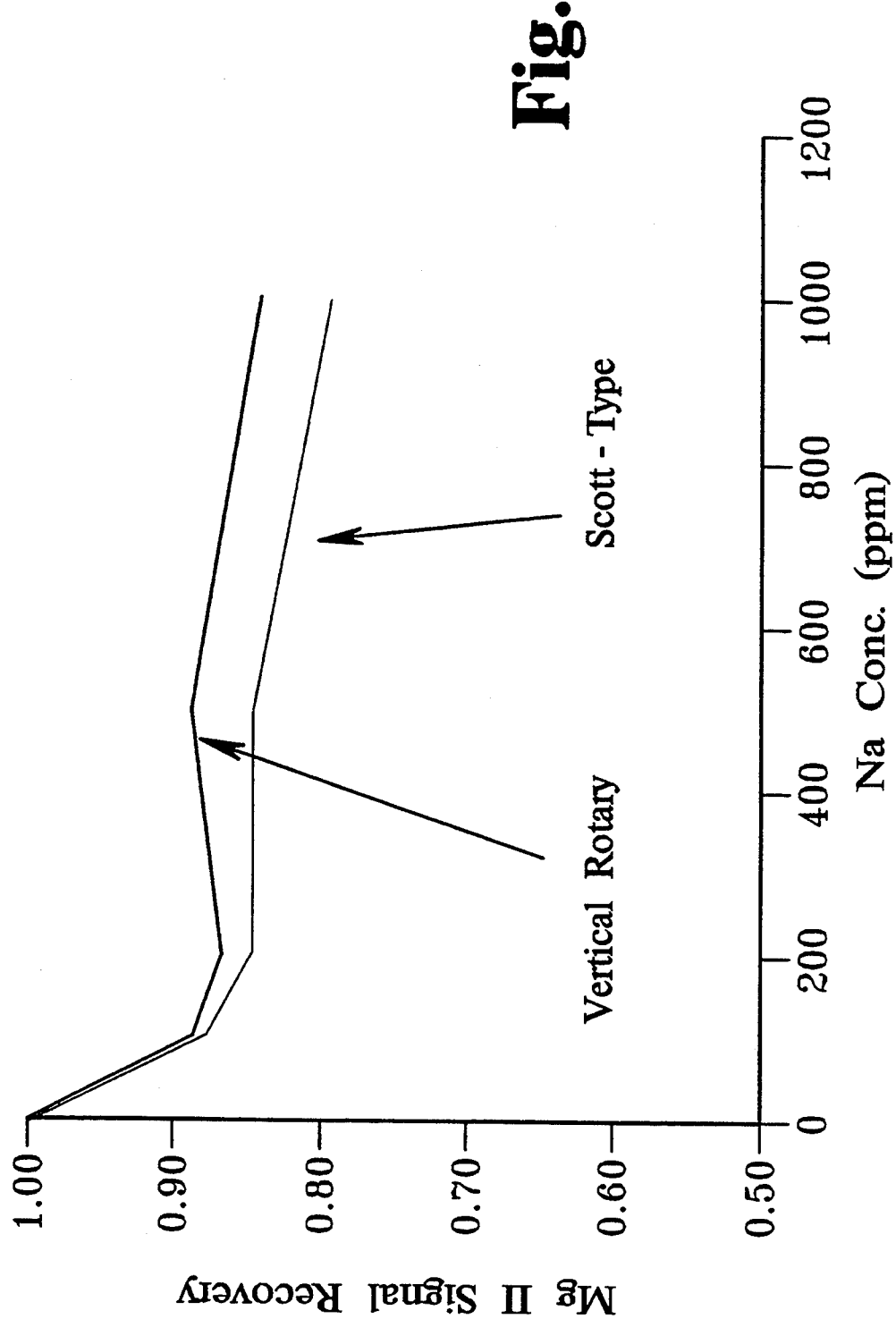
FIG. 5 shows the effect of added Na (as an easily ionized element) on MgII 280.27 nm emission intensity for the Scott-type chamber and a rotary spray chamber of the invention.
Figure 6:
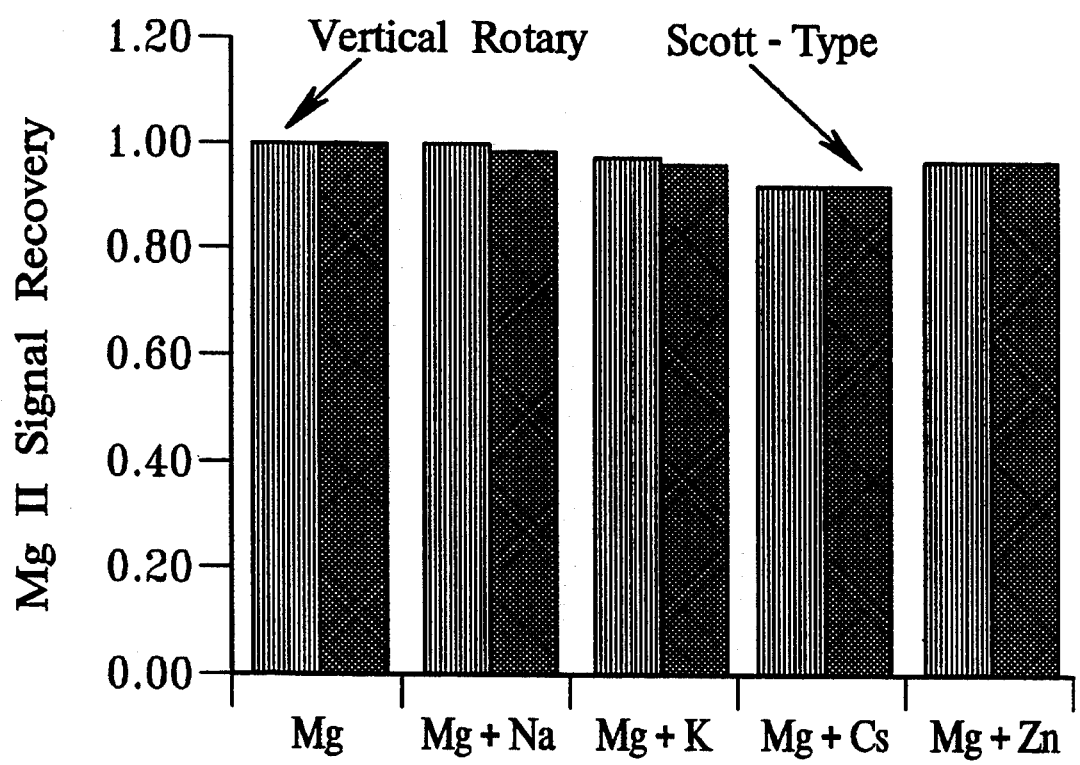
FIG. 6 shows the effect of different matrix elements on MgII 280.27 nm emission intensity.

The effect of an added easily ionized element (EIE) on Mg II 280.27 nm emission (a common and troublesome interference) was assessed under the experimental conditions listed in Table 1 for the 27 MHz ICP-AES. FIG. 5 shows the influence of different concentrations of Na on the Mg II signal, while FIG. 6 illustrates the effect of different EIEs at an equimolar (0.01M) concentration. These plots, show that the EIE interference effects are less severe for the vertical rotary spray chamber.

Simplex Optimization of Mg II 280.27 nm Emission

To verify that the characteristics of the inventive rotary spray chamber are transferable to other ICP torches, power units and photometric systems, the spray chamber was coupled to a larger-diameter (23 mm) torch and employed with an rf supply that is entirely solid-state and powered at 40.68 MHz rather than 27.12 MHz. The photometric system originally employed was replaced by a monochromatic imaging spectrometer equipped for obtaining two-dimensional images of the plasma and for optimizing the plasma operating conditions based on those imaged data (see, C. A. Monnig et al., Spectrochim. Acta, Vol. 43B, pp. 261 (1990)). Details of this alternative configuration are found in Table 1. A simplex algorithm was used to automatically optimize the net Mg II emission signal over assigned ranges of argon carrier flow rate and sample uptake rate (see, L. Ebdon et al., Anal. At. Spectrom. Vol. 4, pp. 505 (1989); and Paul J. Galley et al. "Automated Simplex Optimization for Monochromatic Imaging ICP-AES" Spectrochimica Acta Electronica, in press, 1992). The net signal was obtained through background correction at a nearby spectral location and was the average over the entire imaged plasma region. Although the parameters used in the simplex optimization were limited to the sample uptake rate and the aerosol-carrier Ar flow rate, the optimized conditions for Mg II 280.27 nm produced results (cf. Table 3) similar to those obtained in the single-point measurements described above for the 2 MHz system. In particular, the ratio of the maximum intensities of Mg II emission with the vertical rotary and Scott-type spray chambers is 1.38. This 38% increment is comparable to the signal ratio of 33% recorded in Table 2. Advantageously, the somewhat lower optimal sample uptake rate and carrier-gas flow rate found with the rotary spray chamber would consume slightly less argon and require less sample solution.

Figure 8A:
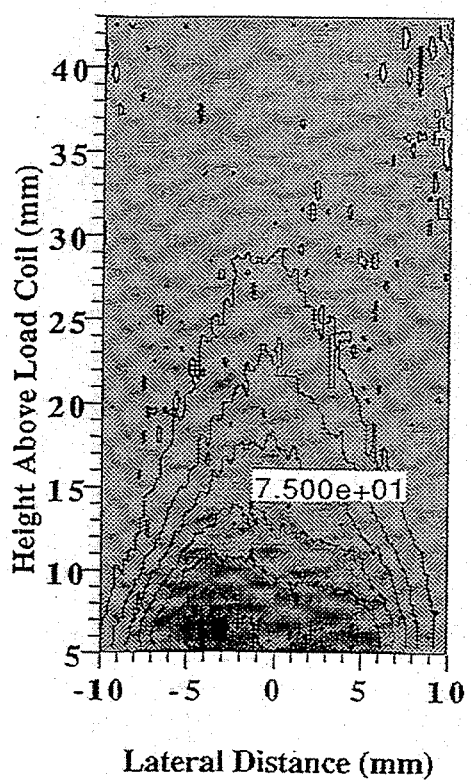
FIG. 8 shows the background emission map taken at 280.27 nm from an optimized 23-mm plasma for the Scott-type 8A (left) and inventive rotary 8B (right) spray chambers.
Figure 8B:
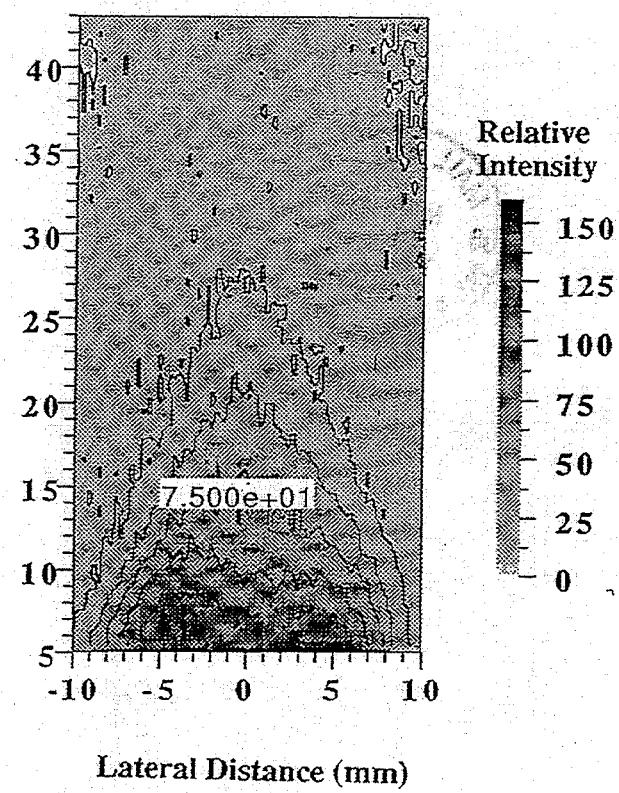

Images of emission from the optimized plasma are shown in FIGS. 7 (Mg II at 280.27 nm) and 8 (background at 280.27 nm). Intensity in arbitrary units. The optimized conditions are 0.54 L/min and 0.50 L/min carrier flow rate for the Scott-type and rotary chambers, respectively, and 1.06 mL/min and 0.91 mL/min sample-uptake rate for the Scott and rotary chamber, respectively. Other conditions for the 40 MHz ICP are listed in Table 1. The images in FIG. 7 verify the overall spatial enhancement of the net Mg II emission signal offered by the inventive rotary spray chamber, while FIG. 8 shows that it produces a background intensity that is somewhat higher at positions low in the plasma but a bit weaker at location high above load coil.

These results demonstrate that the vertical rotary spray chamber is superior to the commonly used Scott spray chamber in the respects of analyte transport efficiency, memory effects, and analytical figures of merit. Compared with the Scott-type device, the vertical rotary spray chamber raises transport efficiency by about 30–50%, reduces wash-out times by a factor of two to three, lowers detection limits threefold, and can be more simply and less costly constructed. Further, it offers slightly better signal-to-background ratios, precision, and susceptibility to interference effects. Small volume rotary spray chambers demonstrate characteristics making them advantageous for application to small-volume sample analysis, and to continuous or discrete sample-introduction approaches such as flow-injection analysis (see, H. Isoyama et al., J. Anal. At. Spectrom. Vol. 4, pp. 351 (1989); and A. J. Ambrose et al., J. Anal. At. Spectrom., Vol. 4, pp. 219 (1989)).

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

TABLE 1

| Plasma Instrumentation and Operating Conditions | | |
|---|---|---|
| | 27.12 MHz ICP | 40 MHz ICP |
| Torch | 18 mm | 23 mm |
| Generator | Plasma Therm RF HFS 5000D | Leco Solid State ICP |
| Power | 0.97 kW | 1.25 kW |
| Frequency | 27.17 MHz | 40.68 MHz |
| Outer Gas Flow | 14.2 L/min | 12 L/min |
| Intermediate Gas Flow | 0.75 L/min | 0.75 L/min |
| Aerosol Gas Flow | 0.70 L/min | 0–1.0 L/min |
| Carrier Argon Pressure | 31.4 psi | 32.0 psi |
| Sample Uptake | 1.5 mL/min | 0–2.11 mL/min |
| 1PZ8 PMT Tube | −900 Volts | −900 Volts |
| Monochromator Slit Width | 30 μm | 100 μm |
| Spectral Bandpass | 0.06 nm | 0.2 nm |
| Object/Image Ratio | 1:1 | Collimated |
| Observation Height ALC | 17.5 mm | 2-D Resolved |
| Sample Solution | 10 μg/mL Mg | 10 μg/mL Mg |
| Data Acquisition | Macintosh IIfx Lab VIEW system | IBM PC 386 |

TABLE 2

| FIGS. of Merit for Two Spray Chambers[a] | | | | | | | | |
|---|---|---|---|---|---|---|---|---|
| | Net MgII Signal (μA) | Bckgrnd Signal (Na) | S/B[b] | S/N$_B$C | RSDS[d] (%) | RSDB[e] (%) | Transport Efficiency (%) | Wash-out Time (s) | Detection[f] Limit (ppb) |
| Double-barrel Scott-Type Spray Chamber | | | | | | | | |
| Mean | 2.13 | 14.4 | 148 | 3268 | 2.31 | 4.73 | 1.9 | 41.9 | 9.5 |
| Std.D. | ±0.01 | ±0.7 | ±70 | ±958 | ±0.24 | ±0.99 | | ±3.0 | ±2.8 |

TABLE 2-continued

| | FIGS. of Merit for Two Spray Chambers[a] | | | | | | | |
|---|---|---|---|---|---|---|---|---|
| | Net MgII Signal (μA) | Bckgrnd Signal (Na) | S/B[b] | S/N_B[c] | RSDS[d] (%) | RSDB[e] (%) | Transport Efficiency (%) | Wash-out Time (s) | Detection[f] Limit (ppb) |
| Vertical Rotary Spray Chamber | | | | | | | | | |
| Mean | 2.84 | 9.4 | 302 | 9150 | 2.26 | 3.31 | 2.8 | 13.8 | 3.3 |
| Std.D. | ±0.03 | ±0.8 | ±38 | ±308 | ±0.02 | ±0.06 | | ±3.7 | ±0.1 |

[a] 10 ppm Mg sample, Mg II 280.27 nm transition line, 17.5 mm above load coil.
[b] S/B = signal to background ratio.
[c] S/N_B = signal to background noise ratio.
[d] RSDS = relative standard deviation of signal.
[e] RSDB = relative standard deviation of blank.
[f] Detection limit = analyte concentration yielding an analytical signal equal to 3 times of the RSDB.

TABLE 3

| Simplex Optimization for 2-D Mg II 280.27 nm Net Emission Intensity | | | | |
|---|---|---|---|---|
| Parameters | Power (kW) | Neb. Flow (L/min) | Uptake (mL/min) | Maximum Signal (arb. unit) |
| Ranges | 1.25 | 0–1.0 | 0.31–2.11 | XXX |
| Optimized Scott | 1.25 | 0.54 | 0.91 | 2056 |
| Optimized Rotary | 1.25 | 0.50 | 1.06 | 2840 |

What is claimed is:

1. A rotary spray chamber device for conditioning an aerosol, comprising:
   chamber walls defining an internal chamber, an inlet opening through which aerosol can be directed into the internal chamber, an exit opening through which conditioned aerosol can exit the chamber, and a drain opening through which large droplets removed from the aerosol and collected as liquid in the chamber can exit therefrom;
   said inlet opening being located such that an aerosol directed into the chamber through the inlet opening tangentially contacts chamber wall areas for imparting a rotary motion to the aerosol within the chamber;
   an impact member extending inwardly into the chamber from a chamber wall location such that the impact member is impacted by the aerosol in its rotary motion, thereby removing large droplets from the aerosol and forming said conditioned aerosol.

2. The rotary spray chamber device of claim 1 which also comprises an inlet tube at said inlet opening, an exit tube at said exit opening, and a drain tube at said drain opening, each said tube fluidly connecting its respective opening to a location exterior of said chamber.

3. The rotary spray chamber device of claim 2 wherein the internal chamber is generally cylindrical in shape.

4. The rotary spray chamber device of claim 3 wherein said chamber walls include a side wall, and the impact member is formed by a dimple in said side wall.

5. The rotary spray chamber device of claim 3 wherein the impact member is positioned such that the aerosol within the chamber rotates substantially about the impact member.

6. The rotary spray chamber of claim 5 wherein said chamber walls are formed from glass.

7. The rotary spray chamber of claim 6 wherein said chamber walls are formed from a borosilicate glass.

8. The rotary spray chamber of claim 6 wherein said inlet tube, exit tube and drain tube are glass and are integrally formed with the chamber walls.

9. A rotary spray chamber for conditioning an aerosol, comprising:
   a hollow generally flattened spheroid member having a pair of opposed side walls and defining a generally cylindrical internal chamber;
   an inlet opening defined in the flattened spheroid member and positioned such that an aerosol directed into the inlet opening substantially tangentially contacts interior surfaces of the walls of the flattened spheroid member, causing the aerosol to rotate within the chamber;
   a dimple member extending inwardly from one of said side walls in a location such that large droplets are removed from the rotating aerosol, thereby forming a conditioned aerosol;
   an exit opening defined in the other of said side walls through which the conditioned aerosol can exit the chamber;
   a drain opening defined in the flattened spheroid member through which large droplets removed from the aerosol and collected as liquid in the chamber can be drained.

10. The rotary spray chamber device of claim 9 which also comprises an inlet tube at said inlet opening, an exit tube at said exit opening, and a drain tube at said drain opening, each said tube fluidly connecting its respective opening to a location exterior of said chamber.

11. The rotary spray chamber of claim 10 wherein the dimple member is formed by a dimple in one of the side walls of the flattened spheroid member.

12. The rotary spray chamber of claim 11 wherein the dimple member is positioned such that the aerosol within the chamber rotates substantially about the dimple member.

13. The rotary spray chamber of claim 12 wherein said flattened spheroid member is formed from glass.

14. The rotary spray chamber of claim 13 wherein said flattened spheroid member is formed from a borosilicate glass.

15. The rotary spray chamber of claim 13 wherein said inlet tube, exit tube and drain tube are glass and are integrally formed with the prolate spheroid member.

16. An apparatus for conditioning a liquid sample for analysis, comprising:
   (i) a nebulizer adapted to form an aerosol from the liquid sample;
   (ii) a rotary spray chamber for conditioning the aerosol, the rotary spray chamber including:
      chamber walls defining an internal chamber and an inlet opening into the internal chamber;
      said inlet opening being located such that an aerosol directed into the chamber through the inlet opening contacts chamber wall areas which impart a rotary motion to the aerosol within the chamber;

an impact member extending inwardly into the chamber from a chamber wall location such that the impact member is impacted by the aerosol in its rotary motion., thereby removing large droplets therefrom and forming a conditioned aerosol;

an exit opening defined by the chamber walls, spaced from said inlet opening, and through which the conditioned aerosol can exit the chamber; and a drain opening defined by the chamber walls, spaced from said inlet opening and said exit opening, and through which large droplets removed from the aerosol and collected as liquid in the chamber can exit the chamber; and (iii) means for directing the aerosol from the nebulizer into the inlet opening of the rotary spray chamber.

17. The apparatus of claim 16 comprising:

a hollow generally flattened spheroid member having a pair of opposed side walls and defining said internal chamber;

said inlet opening being defined in the flattened spheroid member and positioned such that an aerosol directed into the inlet opening substantially tangentially contacts interior surfaces of the walls of the flattened spheroid member, thereby imparting said rotary motion.

18. The apparatus of claim 17 wherein the rotary spray chamber also comprises an inlet tube at said inlet opening, an exit tube at said exit opening, and a drain tube at said drain opening, each said tube fluidly connecting its respective opening to a location exterior of said chamber.

19. The apparatus of claim 18 wherein the impact member is formed by a dimple in one of the side walls of the flattened spheroid member.

20. The apparatus of claim 19 wherein the impact member is positioned such that the aerosol within the chamber rotates substantially about the impact member.

21. The apparatus of claim 20 wherein said flattened spheroid member is formed from glass.

22. The apparatus of claim 21 wherein said flattened spheroid member is formed from a borosilicate glass.

* * * * *

UNITED STATES PATENT AND TRADEMARK OFFICE
CERTIFICATE OF CORRECTION

PATENT NO. : 5,335,860
DATED : August 9, 1994
INVENTOR(S) : Gary M. Hieftje, et al It is certified that error appears in the above-indentified patent and that said Letters Patent is hereby corrected as shown below:

Column 10, line 53 (or in Table 1, line 14 of that table), in between the "P" and the "8", please delete --Z-- and insert 2.

Signed and Sealed this

Twenty-ninth Day of November, 1994

Attest:

BRUCE LEHMAN

Attesting Officer                Commissioner of Patents and Trademarks